United States Patent
Lai et al.

(10) Patent No.: US 12,263,226 B1
(45) Date of Patent: Apr. 1, 2025

(54) NERATINIB-CYCLODEXTRIN COMPOSITION AND METHOD FOR PREPARING SAME

(71) Applicant: Hangzhou Jitai Pharmaceutical Technology Co., Ltd, Hangzhou (CN)

(72) Inventors: Qinghai Lai, Hangzhou (CN); Jing Xu, Hangzhou (CN); Bingxu Zhang, Hangzhou (CN)

(73) Assignee: Hangzhou Jitai Pharmaceutical Technology Co., Ltd., Zhejiang (CN)

( * ) Notice: Subject to any disclaimer, the term of this patent is extended or adjusted under 35 U.S.C. 154(b) by 0 days.

(21) Appl. No.: 18/643,422

(22) Filed: Apr. 23, 2024

Related U.S. Application Data (63) Continuation of application No. PCT/CN2024/086956, filed on Apr. 10, 2024.

(51) Int. Cl.
*A61K 47/69* (2017.01)
*A61K 47/10* (2017.01)
*A61P 1/12* (2006.01)

(52) U.S. Cl.
CPC .......... *A61K 47/6951* (2017.08); *A61K 47/10* (2013.01); *A61P 1/12* (2018.01)

(58) Field of Classification Search
None
See application file for complete search history.

(56) References Cited

U.S. PATENT DOCUMENTS

2023/0285306 A1* 9/2023 Tabuteau ............ C08B 37/0015

FOREIGN PATENT DOCUMENTS

| CN | 110051859 B | | 6/2020 |
| CN | 116473923 A | | 7/2023 |
| IN | 202141028247 | * | 7/2021 |
| JP | 02300140 | * | 5/1989 |

* cited by examiner

*Primary Examiner* — Melissa S Mercier
(74) *Attorney, Agent, or Firm* — FOX ROTHSCHILD LLP (57) ABSTRACT

The present invention discloses a composition comprising neratinib, or a pharmaceutically acceptable salt thereof, and hydroxypropyl-β-cyclodextrin, a method for preparing same, and use thereof. Study results show that the present invention can not only significantly improve the bioavailability of the active ingredient, but also eliminate food effects and adverse event diarrhea.

20 Claims, 1 Drawing Sheet

NERATINIB-CYCLODEXTRIN COMPOSITION AND METHOD FOR PREPARING SAME

TECHNICAL FIELD

The present invention relates to the field of pharmaceutical formulations, and in particular, to a neratinib-cyclodextrin composition, a method for preparing same, and use thereof.

BACKGROUND

Neratinib maleate is an anti-tumor drug. A neratinib maleate tablet of PUMA BIOTECHNOLOGY INC was approved by the U.S. Food and Drug Administration (FDA) On Jul. 17, 2017, under the trade name Nerlynx for the treatment and intensive adjuvant therapy of early breast cancer.

Neratinib is the first and only micromolecular drug for the intensive adjuvant therapy of HER2-positive early breast cancer. As an intracellular kinase inhibitor, neratinib irreversibly binds to epidermal growth factor receptor (EGFR), HER2, and HER4. It not only can reduce EGFR and HER2 autophosphorylation and inhibit the downstream MAPK and AKT signaling pathways, but also exhibits anti-tumor activity in EGFR- and/or HER2-expressing cancer cell lines. Furthermore, the metabolites of neratinib in humans, M3, M6, M7 and M11, also demonstrate activity for inhibiting EGFR, HER2, and HER4.

Food effects on the currently approved neratinib tablet are significant. Due to the low bioavailability (<17%) of neratinib in fasting conditions in humans, a high-fat meal is required to improve the bioavailability, and the dietary nutrients include 50% of carbohydrate, 35% of fat, and 15% of protein, with a total energy of greater than 3200 kcal. Otherwise, the area under curve (AUC) of neratinib may be decreased by 2.2 times. The administration of the drug imposes harsh requirements on breast cancer patients, since the energy in a regular diet may not be strictly calculated and some patients may experience nausea and decreased appetite or even reject such a diet. Insufficient intake of the diet may lead to a decrease in bioavailability, which in turn affects the efficacy and thus the condition of the patients.

According to clinical studies, the approved neratinib tablet may lead to serious gastrointestinal adverse events. The incidence rate is 95% for diarrhea and 39.9% for grade 3-4 diarrhea. The life quality of patients is seriously compromised, and long-term diarrhea may also cause symptoms such as dehydration, nausea, weakness, fatigue, and the like. In addition, due to the development of serious diarrhea events, the administration frequency in 26.4% of the patients was reduced, and 16.8% of the patients withdrew, which resulted in great challenges in ensuring the efficacy and survival of patients.

CN106831710, CN116473923, WO2018134843, and other patents disclose solid dispersions of neratinib or neratinib maleate with different macromolecular carriers. However, none discloses data or protocol for eliminating food effects and adverse event diarrhea.

Therefore, the development of a pharmaceutical composition with little or no food effects and/or adverse event diarrhea to improve the compliance and life quality of patients becomes an urgent task for drug researchers.

SUMMARY

The present invention is intended to solve the problems in the prior art by providing a neratinib-cyclodextrin composition capable of eliminating food effects and adverse event diarrhea, a method for preparing same, and use thereof.

An aspect of the patent document provides a formulation of neratinib. The formulation includes an active ingredient comprising a therapeutically effective amount of neratinib thereof, or a pharmaceutically acceptable salt thereof, or a hydrate thereof, and cyclodextrin, wherein the active ingredient and the cyclodextrin are in a ratio ranging from about 1:1.6 to about 1:5.0 by weight.

In some embodiments, the active ingredient is neratinib maleate and the cyclodextrin is HP-β-cyclodextrin (also known as 2-hydroxypropyl-β-cyclodextrin). In some embodiments, the neratinib maleate and the HP-β-cyclodextrin are in a ratio ranging from about 1:1.8 to about 1:4.6 by weight. In some embodiments, the neratinib maleate and the HP-β-cyclodextrin are in a ratio ranging from about 1:2.0 to about 1:3.0 by weight. In some embodiments, the neratinib maleate and the HP-β-cyclodextrin are in a ratio ranging from about 1:3.0 to about 1:4.0 by weight. In some embodiments, the neratinib maleate and the HP-β-cyclodextrin are in a ratio ranging from about 1:2.5 to about 1:3.2 by weight.

In some embodiments, the amounts of the neratinib maleate and the HP-β-cyclodextrin are selected so that the formulation is characterized by a ratio between a first $AUC_{0-24h}$ and a second $AUC_{0-24h}$ ranging from about 0.8:1 to about 1.6:1, wherein the first $AUC_{0-24h}$ is obtained when the formulation is administered once a day with high fat diet, and wherein the second $AUC_{0-24h}$ is obtained when the formulation is administered once a day under fasting condition, wherein the first $AUC_{0-24h}$ and the second $AUC_{0-24h}$ are obtained from the same daily dose of the active ingredient. In some embodiments, the ratio between the first $AUC_{0-24h}$ and the second $AUC_{0-24h}$ ranges from about 0.8:1 to about 1:1, wherein the neratinib maleate and the HP-β-cyclodextrin are in a ratio ranging from about 1:2.0 to about 1:3.0 by weight. In some embodiments, the ratio between the first $AUC_{0-24h}$ and the second $AUC_{0-24h}$ ranges from about 1:1 to about 1.6:1, wherein the neratinib maleate and the HP-β-cyclodextrin are in a ratio ranging from about 1:3.0 to about 1:4.6 by weight.

In some embodiments, the formulation is administered at a daily dose ranging from about 200 mg to about 300 mg in terms of neratinib.

In some embodiments, the formulation is configured and the amounts of neratinib maleate and HP-β-cyclodextrin are selected so that the first $AUC_{0-24h}$ ranges from about 550 to about 700 ng*h/mL.

In some embodiments, the amounts of the neratinib maleate and the HP-β-cyclodextrin are selected so that the formulation is characterized by a ratio between a first $C_{max}$ and a second $C_{max}$ ranging from about 0.9:1 to about 1.5:1, wherein the first $C_{max}$ is obtained when the formulation is administered once a day with high fat diet, and wherein the second $C_{max}$ is obtained when the formulation is administered once a day under fasting condition, wherein the first $C_{max}$ and the second $C_{max}$ are obtained from the same daily dose of the active ingredient.

In some embodiments, the amounts of neratinib maleate and HP-β-cyclodextrin are selected so that the first $C_{max}$ ranges from about 40 to about 80 ng/ml when the formulation is administered with high fat diet. In some embodiments, the neratinib maleate and the HP-β-cyclodextrin form a clathrate.

In some embodiments, the formulation further comprises polyvinyl caprolactam-polyvinyl acetate-polyethylene glycol graft copolymer (PCL-PVAc-PEG or Soluplus). In some embodiments, the ratio by weight between neratinib maleate and PCL-PVAc-PEG in the formulation is about 1:0.2 to about 1:0.3. In some embodiments, the neratinib maleate and the HP-β-cyclodextrin are in a ratio ranging from about 1:2.0 to about 1:4.0 by weight.

In some embodiments, the amounts of neratinib maleate and HP-β-cyclodextrin are selected so that the formulation has less than 50% chance of diarrhea when administered once a day to a subject.

Another aspect provides a method of reducing risk of diarrhea in a human patient being treated with neratinib, comprising administering to the subject a formulation disclosed herein.

Another aspect provides a method of treating breast cancer in a human patient, comprising administering to the subject a formulation disclosed herein.

DETAILED DESCRIPTION

Various embodiments herein disclose pharmaceutical compositions or dosage forms of neratinib or a pharmaceutically acceptable salt thereof. In comparison with previously reported dosage forms, the compositions or dosage forms of this patent document have the advantage of significantly improved bioavailability under fasting condition or without a high fat diet. Meanwhile, incidences of adverse events such as diarrhea have been eliminated or reduced.

Although the following contents may refer to or exemplify a specific embodiment of a pharmaceutical composition or dosage form, they are not limited to the specified ranges of the pharmaceutical composition or dosage form. In view of practicality and economy considerations, a person skilled in the art can make various modifications to, e.g., the amounts of the active ingredient and the excipients, and the dosage regimen of the dosage form for treating diseases or disorders.

Unless otherwise defined, all technical and scientific terms used herein have the same meaning as commonly understood by a person skilled in the field of the present invention. In case of conflict, the definitions provided in the application prevail.

The term "a", "an" or "the" as used herein means "one or more" or "at least one". That is, reference to any element or composition of the present invention by "a", "an" or "the" does not exclude the possibility of the presence of a plurality of the elements and compositions.

The term "about" and the like as used herein, when used in connection with a numerical variable, generally means that the value of the variable and all values of the variable are within the range of experimental error (e.g., within the 95% confidence interval for the mean) or within +10% or within +5% of the indicated value.

The term "AUC0-24 h" refers to the area under the concentration-time curve (AUC) from the time of dosing (time 0) to the 24 h. Unless otherwise specified, AUC0-24 h and $C_{max}$ are obtained after a single dose administration.

The term "bioequivalence" or "bioequivalent" refers to two formulations, dosage forms, products, or compositions of an active ingredient having biological equivalence. It is generally considered bioequivalent if the 90% Confidence Interval ("CI") of the relative mean $C_{max}$, $AUC_{(0-t)}$ and $AUC_{(0-last)}$ of the test formulation to reference formulation (i.e., brand product) is within 80.0% to 125.0% in the same testing state (e.g. high-fat diet or fasting condition) of a tested subject.

The term "high fat diet" or "high fat meal" refers generally to a meal of at least about 700 kcal and at least about 45% fat (relative percentage of kcal which are fat), or alternatively at least about 900 kcal and at least about 50% fat. The term "high fat food" refers generally to a food comprising at least 20 g of fat, or at least 25, 30, 35, 40, 45, or 50 g of fat, and/or at least about 45% or 50% fat. One FDA Guidance defines a "high-fat meal" as approximately 50% of total caloric content of the meal, whereas a "high-calorie meal" is approximately 800 to 1000 calories. The FDA recommends a high-fat and high-calorie meal as a test meal for food-effect bioavailability and fed bioequivalence studies. This test meal should derive approximately 150, 250, and 500-600 calories from protein, carbohydrate and fat, respectively. An example test meal consists of two eggs fried in butter, two strips of bacon, four ounces of hash brown potatoes and eight ounces of whole milk. Substitution is possible if a similar amount of calories from protein, carbohydrate, and fat has comparable meal volume and viscosity (Guidance for Industry, Food-Effect Bioavailability and Fed Bioequivalence Studies, U.S. Department of Health and Human Services, Food and Drug Administration, Center for Drug Evaluation and Research (CDER), December 2002). In some embodiments, a formulation administered with a high-fat diet means that the formulation is taken within 30 minutes, 25 minutes, 20 minutes, 15 minutes, 10 minutes, or 5 minutes after ingestion of a meal, or taken simultaneously with the high-fat diet.

The term "neratinib", "active pharmaceutical ingredient", or "active ingredient" as used herein refers to the compound (E)-N-[4-[3-chloro-4-(pyridin-2-ylmethoxy) anilino]-3-cyano-7-ethoxyquinolin-6-yl]-4-(dimethylamino) but-2-enamide (CAS 698387 Sep. 6).

The term "pharmaceutically acceptable salt" refers to a salt of the active ingredient. The salt form retains the desired biological activity of the parent compound and does not impart any undesired toxicological effects. The pharmaceutically acceptable salt may be an inorganic acid salt, an organic acid salt, or a metal salt. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid.

The term "subject" as used herein is intended to include human and non-human animals. Non-human animals include all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the immune response.

An aspect of the patent document provides a pharmaceutical composition or formulation comprising a therapeutically effective amount of neratinib or a pharmaceutically acceptable salt thereof and cyclodextrin. With or without a high fat diet, the composition or formulation provides a suitable $AUC_{(0-last)}$ and $C_{max}$. In addition, the composition or formulation is able to achieve bioequivalence with the market drug Nerlynx with the same dosage. Different from Nerlynx, however, the composition disclosed here overcomes or reduces size effects such as diarrhea. In some embodiments, neratinib is in a maleate salt form. In some embodiments, the cyclodextrin (CD) is selected from HP-β-CD, α-CD, β-CD, γ-CD, RM-β-CD, HP-γ-CD, SBE-β-CD. In some embodiments, the cyclodextrin is HP-β-CD.

The pharmaceutical composition or formulation disclosed herein may in any suitable dosage form, including for example, tablets, pills, dragees, capsules, liquids, gels, syrups, slurries, suspensions and the like, for administration to a subject in need.

The ratio between neratinib or its salt (e.g. maleate salt) and the cyclodextrin (e.g. HP-β-cyclodextrin) may range from about 1:1.1 to about 1:5.0, from about 1:1.1 to about 1:4.8, from about 1:1.2 to about 1:4.8, from about 1:1.4 to about 1:4.8, from about 1:1.6 to about 1:4.6, from about 1:1.8 to about 1:4.6, from about 1:1.6 to about 1:4.4, from about 1:1.8 to about 1:4.2, from about 1:1.8 to about 1:4.0, from about 1:2.0 to about 1:4.0, from about 1:2.0 to about 1:3.8, from about 1:2.0 to about 1:3.6, from about 1:2.0 to about 1:3.4, from about 1:2.0 to about 1:3.2, from about 1:2.2 to about 1:3.4, from about 1:2.2 to about 1:3.2, from about 1:2.4 to about 1:3.2, from about 1:2.5 to about 1:3.2, by weight. Nonlimiting examples of the ratio include 1:1.0, 1:1.2, 1:1.4, 1:1.6, 1:1.8, 1:2.0, 1:2.2, 1:2.4, 1:2.5, 1:2.6, 1:2.8, 1:3.0, 1:3.2, 1:3.4, 1:3.6, 1:3.8, 1:4.0, 1:4.2, 1:4.4, 1:4.6, 1:4.8, 1:5.0, and any range between any two of the aforementioned ratios. Preferably, the neratinib or its salt form (e.g. maleate salt) and the cyclodextrin (e.g. HP-β-cyclodextrin) form a clathrate, where the active ingredient is trapped or enclosed within the framework of the cyclodextrin. The amount of neratinib or its salt (e.g. maleate salt) in the composition or formulation may be 1%, 2%, 5%, 8%, 15%, 20%, 25%, 30%, 40%, 50%, 60%, 70%, 80% by weight or any range between any two of the aforementioned values.

In some embodiments, the ratio between neratinib maleate and HP-β-cyclodextrin ranges from about 1:1.1 to about 1:5.0, from about 1:1.5 to about 1:5.0, from about 1:1.6 to about 1:4.8, from about 1:1.8 to about 1:4.8, from about 1:2.5 to about 1:3.5, or from about 1:2 to about 1:5.0 by weight. Nonlimiting examples of the ratio include 1:1.2, 1:1.4, 1:1.6, 1:1.8, 1:2.0, 1:2.2, 1:2.4, 2.5, 1:2.6, 1:2.8, 1:3.0, 1:3.2, 1:3.4, 1:3.6, 1:3.8, 1:4.0, 1:4.2, 1:4.4, 1:4.6, 1:4.8, 1:5.0, and any range between any two of the aforementioned ratios. In some embodiments, the ratio is 1:2.2, 1:2.4, 1:2.5, 1:2.6, 1:2.8, 1:3.0, 1:3.2, or any range between any two of them.

The amount of active ingredient in a unit dosage form of the formulation disclosed herein may range from about 20 to about 400 mg, from about 20 to about 300 mg, from about 30 to about 300 mg, from about 40 to about 240 mg, from about 40 to about 200 mg, from about 40 to about 160 mg, from about 40 to about 120 mg, from about 40 to about 80 mg, or about 40 to about 60 mg. The amount of neratinib or its pharmaceutically acceptable salt (e.g. maleate salt) in the formulation ranges from about 10 to about 500 mg, from about 10 to about 400 mg, from about 20 to about 300 mg, from about 40 to about 240 mg, from about 20 to about 200 mg, from about 30 to about 200 mg, from about 30 to about 180 mg, or from about 40 to about 160 mg. Nonlimiting examples of neratinib or its pharmaceutically acceptable salt in the composition or formulation include 10, 20, 30, 40, 50 60, 80, 100, 120, 140, 150, 160, 180, 200, 240, 250, 300 mg and any range between any two of the aforementioned values (in mgs). In some embodiments, the composition or formulation contains 20, 40, 60, 80, 160, 200, 240 or 300 mg of neratinib. The composition or formulation can be administered once a day, twice a day, three times a day or as prescribed by a medical professional. In some embodiments, the composition or formulation is administered at a daily dosage of 120, 160, 240 or 300 mg of neratinib or its salt (e.g. maleate).

The composition or formulation described herein may contain one or more additional excipients including for example solubility enhancer, surfactant, binder, filler, disintegrant, glidant, lubricant and other polymer excipients. The amount of cyclodextrin and other excipient in the composition or formulation may each independently be 1%, 2%, 5%, 8%, 15%, 20%, 25%, 30%, 40%, 50%, 60%, 70%, 80% by weight or any range between any two of the aforementioned values.

Nonlimiting examples of fillers include starch, dextrin, sucrose, Sorbitol, Sodium Saccharin, Acesulfame potassium, Xylitol, Aspartame, Mannitol, starch, PVP (polyvinyl pyrrolidone), low molecular weight HPC (hydroxypropyl cellulose), microcrystalline cellulose (MCC), low molecular weight HPMC (hydroxypropyl methylcellulose), low molecular weight carboxymethyl cellulose, ethylcellulose, dicalcium phosphate, silicified microcrystalline cellulose, alginates, gelatin, polyethylene oxide, acacia, dextrin, sucrose, magnesium aluminum silicate, and polymethacrylates. Fillers also include agents such as microcrystalline cellulose, starch, lactitol, lactose, a suitable inorganic calcium salt, sucrose, glucose, mannitol, silicic acid, or a combination thereof.

Nonlimiting examples of disintegrants include agar, calcium carbonate, potato or tapioca starch, alginic acid, certain silicates, sodium carbonate, crospovidone (cross-linked PVP), sodium carboxymethyl starch (sodium starch glycolate), cross-linked sodium carboxymethyl cellulose (croscarmellose), pregelatinized starch (starch 1500), microcrystalline starch, water insoluble starch, sodium starch glycolate, potassium polacrilin, sodium alginate, calcium carboxymethyl cellulose, magnesium aluminum silicate (Veegum) or a combination thereof.

Nonlimiting examples of glidants include colloidal silicon dioxide, talc, magnesium carbonate, calcium silicate, fumed silicon dioxide, and combinations thereof.

Nonlimiting examples of lubricants include for example stearates, sodium stearyl fumarate, magnesium salts and magnesium stearate.

Nonlimiting examples of surfactants include Tween, solutol HS 15, hexadecyl trimethyl ammonium bromide, vitamin E polyethylene glycol succinate, ethoxylated hydrogenated castor oil, poloxamer, sodium dodecyl sulfate.

Other nonlimiting examples of polymer excipients include Eudragit L, Eudragit S, Eudragit R, Eudragit RS, Eudragit NE, Eudragit FS, PEG 200-8000, polyvinylketone, copovidone, cyclodextrin, PCL-PVAc-PEG, Cellacefate, hydroxypropyl methyl cellulose, microcrystalline cellulose, hydroxypropylmethylcellulose, and acetatesuccinate.

In some embodiments, the composition or formulation disclosed herein further includes Soluplus (PCL-PVAc-PEG), Soluplus is a trade name for a copolymer of vinyl caprolactam, vinyl acetate, and polyethylene glycol (PEG). The chemical structure of PCL-PVAc-PEG consists of these three main components linked together in a copolymer chain. Specifically, it is a graft copolymer where polyethylene glycol (PEG) is grafted onto a backbone composed of vinyl caprolactam and vinyl acetate units. The chemical structure of PCL-PVAc-PEG can be represented as Poly (vinyl caprolactam)-co-(vinyl acetate)-g-polyethylene glycol. The ratio by weight between neratinib or its salt (e.g. maleate salt) and PCL-PVAc-PEG in the formulation ranges from about 1:0.10 to about 1:0.50, from about 1:0.15 to about 1:0.40, from about 1:0.20 to about 1:0.35, from about 1:0.25 to about 1:0.30, or from about 1:0.22 to about 1:0.28 by weight. Nonlimiting examples of the ratio include 1:0.10, 1:0.15, 1:0.20, 1:0.22, 1:0.24, 1:0.25, 1:0.26, 1:0.28, 1:0.30, 1:0.32, 1:0.35, 1:0.40, and any range between any two of the aforementioned ratios. In some embodiments, the ration between the neratinib or its salt form (e.g. maleate salt) and the cyclodextrin (e.g. HP-β-cyclodextrin) is 1:1.8, 1:2.0, 1:2.2, 1:2.4, 1:2.5, 1:2.6, 1:2.8, 1:3.0, 1:3.2, 1:3.6, 1:3.8, 1:4.0, 1:4.2, 1:4.4, 1:4.6, or any range between any two of the aforementioned ratios. In some embodiments, the ratio among the neratinib or its salt form (e.g. maleate salt), the cyclodextrin (e.g. HP-β-cyclodextrin) and PCL-PVAc-PEG is about 1:2.5:0.25. In some embodiments, the neratinib maleate and the HP-β-cyclodextrin are in a ratio ranging from about 1:3.0 to about 1:4.0 by weight. In some embodiments, the neratinib maleate and the HP-β-cyclodextrin are in a ratio ranging from about 1:2.5 to about 1:3.2 by weight.

By adjusting the ratio and amounts of the active ingredient and the excipients, the pharmacokinetic profile and other properties of the composition or formulation can be controlled. In the context of administering a drug, food effect resulting from a high-fat diet or no-high fat diet (e.g. fasting condition) can be reflected in significant differences in AUC, $C_{max}$ or other pharmaceutically relevant properties.

In some embodiments, a non-high fat diet refers to a diet or meal that has a lower level of calorie and/or lower level of fat than a high-fat diet defined above. In some embodiments, a formulation taken with a non-high fat diet also refers to the formulation being administered at a time sufficiently away from the ingestion of a high-fat meal or diet, for example, by being earlier or later than the a high-fat meal by at least 1 hour, at least 1.5 hours, at least 2 hours, at least 2.5 hours, at least 3 hours, at least 4 hours or at least 5 hours. In some embodiments, a formulation taken with a non-high fat diet also refers to the formulation being administered under fasting condition, which refers to a physiological state in which an individual abstains from consuming food or caloric beverages for a specified period before and after drug administration. Typically, this involves refraining from eating for a minimum duration of 8 to 12 hours prior to drug intake, ensuring that the gastrointestinal tract is empty and basal metabolic processes are predominant. Fasting conditions are employed to minimize potential interactions between drugs and food, as well as to optimize drug absorption by reducing interference from the digestion and absorption of nutrients. Understanding the implications of non-high fat diel or fasting on drug pharmacokinetics is essential for determining appropriate dosing regimens and maximizing therapeutic outcomes.

In some embodiments, the formulation or composition is configured, the amounts of the ingredient and excipients, and/or the ratio between neratinib or its salt (e.g. maleate) and cyclodextrin (e.g. HP-β-cyclodextrin) are selected so that the formulation or composition, when administered under fasting condition or non-high fat diet condition, provides an AUC(0-last) ranging from about 400 to about 750, from about 450 to about 720, from about 480 to about 700, from about 450 to about 550, or from about 460 to about 520 ng*h/mL. Further nonlimiting examples of the $AUC_{0-24h}$ include 400, 420, 440, 450, 460, 470, 480, 490, 500, 510, 520, 530, 540, 550, 560, 580, 600, 620, 640, 660, 680, 700, 720, 740 ng*h/mL, and any range between any two of the aforementioned values.

In some embodiments, the formulation or composition is configured, the amounts of the ingredient and excipients, and/or the ratio between neratinib or its salt (e.g. maleate) and cyclodextrin (e.g. HP-β-cyclodextrin) are selected so that the formulation or composition, when administered under fasting condition or non-high fat diet condition, provides a $C_{max}$ ranging from about 30 to about 120, from about 35 to about 110, from about 40 to about 100, from about 35 to about 98, from about 38 to about 95, from about 35 to about 90, from about 40 to about 85, from about 40 to about 75, from about 40 to about 70, from about 40 to about 65, from about 40 to about 60, from about 40 to about 55, from about 40 to about 50, or from about 40 to about 45 ng/ml. Further nonlimiting examples of the $C_{max}$ include 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 10, 105, 110 ng/mL, and any range between any two of the aforementioned values.

In some embodiments, the formulation or composition is configured, the amounts of the ingredient and excipients, and/or the ratio between neratinib or its salt (e.g. maleate) and cyclodextrin (e.g. HP-β-cyclodextrin) are selected so that the formulation or composition, when administered with a high fat diet, provides an AUC(0-last) ranging from about 500 to about 1,200, from about 500 to about 1,100, from about 500 to about 1,000, from about 550 to about 950, from about 550 to about 900, from about 550 to about 800, about 550 to about 750, about 550 to about 700, or from about 550 to about 650 ng*h/mL. Further nonlimiting examples of the $AUC_{0-24h}$ include 500, 520, 550, 600, 650, 700, 750, 800, 850, 900, 950, 1,000, 1,100 ng*h/mL and any range between any two of the aforementioned values.

In some embodiments, the formulation or composition is configured, the amounts of the ingredient and excipients, and/or the ratio between neratinib or its salt (e.g. maleate) and cyclodextrin (e.g. HP-β-cyclodextrin) are selected so that the formulation or composition, when administered with a high fat diet, provides a $C_{max}$ ranging from about 30 to about 120, from about 35 to about 110, from about 40 to about 100, from about 35 to about 98, from about 38 to about 95, from about 35 to about 90, from about 40 to about 85, from about 40 to about 75, from about 40 to about 70, from about 40 to about 65, from about 40 to about 60, from about 40 to about 55, from about 40 to about 50, or from about 40 to about 45 ng/mL. Further nonlimiting examples of the $C_{max}$ include 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 10, 105, 110 ng/mL, and any range between any two of the aforementioned values.

The composition or the formulation of this patent document can effectively reduce food effect on pharmacokinetics of the active ingredient. The impact on reduced food effect can be characterized as a ratio between a first AUC(0-last)

or $C_{max}$ and a second $C_{max}$. The first AUC(0-last) or $C_{max}$ is the mean area-under-the curve or mean maximum plasma concertation when the formulation is administered with a high fat diet, and the second AUC(0-last) or $C_{max}$ is the mean area-under-the curve or mean maximum plasma concertation when the formulation is administered under fasting condition. In some embodiments, the composition or the formulation is configured and the amounts of neratinib maleate and cyclodextrin are selected so that the ratio between the first $C_{max}$ and the second $C_{max}$ ranges from about 0.8 to about 1.6, from about 0.9 to about 1.5, from about 0.9 to about 1.4, from about 1.0 to about 1.4, from about 1.1 to about 1.3. Nonlimiting examples of the ratio include about 0.80, about 0.85, about 0.90, about 0.95, about 1.0, about 1.1, about 1.2, about 1.3, about 1.4, about 1.6, or any range between any two of the aforementioned ratios.

In some embodiments, the composition or the formulation is configured and the amounts of neratinib maleate, cyclodextrin and other excipients are selected so that a bioequivalence with brand name product is achieved. The ratio between the formulation and the brand name product (e.g. Nerlynx) of the same dosage in terms of AUC(0-last) or $C_{max}$ independently ranges from about 0.8 to about 1.6, from about 0.9 to about 1.5, from about 0.9 to about 1.4, from about 1.0 to about 1.4, from about 1.1 to about 1.3. Nonlimiting examples of the ratio include about 0.80, about 0.85, about 0.90, about 0.95, about 1.0, about 1.1, about 1.2, about 1.3, about 1.4, or any range between any two of the aforementioned ratios.

In some embodiments, the amounts of neratinib maleate and HP-β-cyclodextrin are selected so that the first $C_{max}$ ranges from about 5 to about 200, from about 10 to about 200, from about 40 to about 150, from about 100 to about 150, from about 40 to about 80, from about 50 to about 70 or from about 35 to about 70 ng/ml when the formulation is administered once a day with high fat diet. In some embodiments, the first $C_{max}$ is obtained after a single dose of administration. Nonlimiting examples of the first $C_{max}$ include 2, 5, 10, 20, 25, 30, 40, 50, 60, 80, 100, 120, 150, 200 ng/ml and any range between any two of the aforementioned values.

In some embodiments, the amounts of neratinib maleate and HP-β-cyclodextrin are selected so that $AUC_{0-24h}$ ranges from about 100 to about 2000, from about 200 to about 2000, from about 300 to about 1500, from about 500 to about 1500, from about 500 to about 1000, from about 600 to about 800 or from about 450 to about 550 ng/ml. In some embodiments, the formulation is administered as a single dose. In some embodiments, the formulation is administered with high fat diet. In some embodiments, the formulation is administered under fasting condition. Nonlimiting examples of the $AUC_{0-24h}$ include 100, 200, 300, 400, 450, 500, 550, 600, 650, 700, 750, 800, 850, 900, 1000, 1200, 1400, 1500, 1800, 2000 ng*h/mL and any range between any two of the aforementioned values.

Another aspect of the patent document provides a method of treating breast cancer in a human patient. In some embodiments, the formulation or composition disclosed herein achieves a bioavailability of neratinib maleate in vivo under fasting conditions in the same level as that after a high-fat meal, suggesting a complete elimination of food effects. Therefore, with the composition or formulation disclosed herein, a strictly defined high-fat meal in advance is no longer required, and the administration at any time can meet the bioavailability and/or efficacy requirement.

The method includes administering to the patient a formulation or composition disclosed herein. In some embodiments, the formulation or composition is configured, the amounts of the ingredient and excipients, and/or the ratio between neratinib or its salt (e.g. maleate) and cyclodextrin (e.g. HP-β-cyclodextrin) and other excipients are selected so that the method provides a AUC0-24 h ranging from about 400 to about 1000, from about 400 to about 900, from about 400 to about 850, from about 400 to about 800, from about 400 to about 700, from about 400 to about 600 or from about 450 to about 550 ng*h/mL when the formulation is administered under non-high fat diet or fasting condition. In some embodiments, the formulation or composition is configured, the amounts of the ingredient and excipients, and/or the ratio between neratinib or its salt (e.g. maleate) and cyclodextrin (e.g. HP-β-cyclodextrin) and other excipients are selected so that when the formulation is administered under non-high fat diet or fasting condition, the method provides a $C_{max}$ in a range as disclosed above. In some embodiments, the formulation or composition is configured, and the amounts of the ingredient and excipients, and/or the ratio between neratinib or its salt (e.g. maleate) and cyclodextrin (e.g. HP-β-cyclodextrin) and other excipients are selected so that when the formulation is administered with a high fat diet the method provides a $AUC_{(0-last)}$ in a range as disclosed above. In some embodiments, the formulation or composition is configured, the amounts of the ingredient and excipients, and/or the ratio between neratinib or its salt (e.g. maleate) and cyclodextrin (e.g. HP-β-cyclodextrin) and other excipients are selected so that when the formulation is administered with a high fat diet the method provides a $C_{max}$ in a range as disclosed above.

In some embodiments, the formulation or composition is configured, and the amounts of the ingredient and excipients, and/or the ratio between neratinib or its salt (e.g. maleate) and cyclodextrin (e.g. HP-β-cyclodextrin) and other excipients are selected so that the method minimizes food effect, which is characterized by a ratio between a first AUC(0-last) or $C_{max}$ and a second AUC(0-last) or $C_{max}$ as described above.

In some embodiments, the subject for the above disclosed data and ranges (e.g. AUC(0-last) or $C_{max}$) is human. In some embodiments, the subject for the above disclosed data and ranges (e.g. AUC(0-last) or $C_{max}$) is a commonly used test animal model (e.g. beagle dog).

A related aspect provides a method of reducing adverse events of neratinib in a human patient. The method includes administering to the patient a formulation or composition disclosed herein. In some embodiments, the formulation or composition is configured, and the amounts of the ingredient and excipients, and/or the ratio between neratinib or its salt (e.g. maleate) and cyclodextrin (e.g. HP-β-cyclodextrin) and other excipients are selected so that the method reduces adverse events such as diarrhea by at least 20%, at least 30%, at least 40%, at least 50%, at least 60%, at least 80%, at least 90%, or 100% relative to a reference formulation with the same ingredients and excipients in the same amounts (except without cyclodextrin).

Besides elimination reduction of food effect and reduction of side effects, the composition or formulation disclosed herein also provides better dissolution of neratinib in a neutral environment and increased local concentration of the active ingredient in intestinal tracts, thereby improving the bioavailability. Moreover, the composition has the advantages of cost efficient manufacturing and adaptability for scale-up production.

In some embodiments, the composition or formulation disclosed herein improves solubility of neratinib maleate in neutral conditions (pH 6.5) from 7.4 µg/mL to 48.01 mg/mL (6500 times). In some embodiments, a combination of neratinib maleate and hydroxypropyl-β-cyclodextrin more significantly increases the solubility of neratinib maleate to 324.30 mg/mL (44,000 times). In some embodiments, PCL-PVAc-PEG can be included for synergistic results. For instance, when neratinib maleate, hydroxypropyl-β-cyclodextrin, and PCL-PVAc-PEG are formulated into a ternary composition, the solubility can be increased to 429.75 mg/mL, 58,000 times greater than that of neratinib maleate substance, thereby increasing greatly local concentration of the active ingredient in intestinal tracts and improving the bioavailability.

The neratinib-cyclodextrin composition prepared according to the present invention can be blended with common excipients via a conventional preparation process to provide a neratinib pharmaceutical composition, for example, in granules, tablets, capsules, solutions, injections, and other forms. In preferred embodiments, the neratinib-cyclodextrin composition is present in the formulation in a content of 0.0001-99.9999%, or may be present in an amount of 0.01-1000 mg in one dose (e.g., a capsule or tablet).

The formulation or composition disclosed herein can be prepared by any conventional process. In a preferred condition of the present invention, the composition is preferably prepared by a process comprising spray drying.

In one exemplary embodiment, spray drying comprises:
(1) dissolving neratinib or a pharmaceutically acceptable salt thereof, and cyclodextrin in a hydrophilic organic solvent, an aqueous solution or a buffer at pH 5.0 or lower, or a mixed solvent of any two of the above to give a solution; and
(2) subjecting the solution formed in step (1) to spray drying to give the cyclodextrin composition.

In another exemplary embodiment, the lyophilization comprises:
(1) dissolving neratinib or a pharmaceutically acceptable salt thereof, and cyclodextrin in a hydrophilic organic solvent, an aqueous solution or a buffer at pH 5.0 or lower, or a mixed solvent of any two of the above to give a solution; and
(2) subjecting the solution formed in step (1) to lyophilization to give the cyclodextrin composition.

It will be appreciated that the neratinib-cyclodextrin composition of the present invention can also be prepared by other well-established processes in the art, and various forms of neratinib-cyclodextrin compositions prepared by conventional processes shall fall within the scope of the present invention on the premise of the neratinib-cyclodextrin composition formula of the present invention.

EXAMPLES

The embodiments of the present disclosure will be further described in detail with reference to the following specific examples. It will be appreciated that the following examples are merely exemplary illustrations and explanations of the present disclosure, and should not be construed as limiting the protection scope of the present disclosure. All techniques implemented based on the content of the present disclosure described above are included within the protection scope of the present disclosure.

Unless otherwise stated, the starting materials, originator products, and reagents used in the following examples are all commercially available products, or can be prepared by using known methods.

Preparation Example 1

Preparation of FaSSIF solution (fasted state simulated intestinal fluid, pH 6.5): 0.42 g of NaOH, 3.44 g of $NaH_2PO_4$, and 6.19 g of NaCl were added into a beaker before 900 mL of purified water was added. The pH was adjusted and the volume was brought to 1 L with purified water. 2.24 g of FaSSIF powder was added into the 1-L buffer.

Solubility measurement: 400 μL of the FaSSIF solution was added into a scintillation flask, and a small amount of the neratinib-cyclodextrin composition powder was gradually added at room temperature with magnetic stirring until a precipitate was observed. The addition amount of the powder was recorded. The solubility of neratinib maleate was calculated from the loading amount of the powder. Dissolution measurement of the neratinib maleate substance (API): 400 μL of the FaSSIF solution was added into a scintillation flask. An excessive amount of neratinib maleate substance was added. The mixture was magnetically stirred at room temperature for 48 h, and centrifuged to give a supernatant. The supernatant was filtered and subjected to HPLC and other measurements to give the solubility of neratinib maleate, 0.0074 mg/mL.

Example 1

An appropriate amount of neratinib maleate (API) was transferred to 40 times (W/W) of an aqueous hydrochloric acid solution (pH 1.2). The mixture was stirred until the solids were completely dissolved, and an appropriate amount of HP-β-cyclodextrin was added to the resultant solution in a mass ratio shown in Table 1. The mixture was stirred at room temperature for 30 mins or more to give a clear solution. The solution was then subjected to spray drying to give a loose powder. The inlet temperature of the solution was 200° C., the flow rate was 5.2 mL/min, and the outlet temperature was 100-130° C. The dried powder was then aliquoted into capsules in a loading amount of 40 mg.

The solubility of the clathrate of neratinib and HP-β-cyclodextrin prepared was measured according to the solubility measurement in Preparation Example 1. The results are shown in Table 1.

TABLE 1

| No. | API:HP-β-cyclodextrin (w/w) | API solubility (mg/mL) | Increasing factor (×10,000) |
| --- | --- | --- | --- |
| 1 | 1:1.1 | 227.8 | 3.1 |
| 2 | 1:2.5 | 360.31 | 4.9 |
| 3 | 1:4.6 | 461.15 | 6.2 |

It can be seen from the above results that when the mass ratio of neratinib to HP-β-cyclodextrin was 1:1.1, the solubility of the clathrate of neratinib and HP-β-cyclodextrin was 31,000 times that of neratinib maleate, and the solubility increased correspondingly with the increase in the amount of HP-β-cyclodextrin.

Example 2

An appropriate amount of neratinib maleate (API) was transferred to 40 times (W/W) of an aqueous hydrochloric acid solution (pH 1.2). The mixture was stirred until the solids were completely dissolved, and an appropriate amount of HP-β-cyclodextrin was added to the resultant solution. The mixture was stirred at room temperature for 30 mins or more to give a clear solution or a suspension. The solution or suspension was then lyophilized to give a loose powder, which was then aliquoted into capsules in a loading amount of 40 mg.

The solubility of the clathrate of neratinib and HP-β-cyclodextrin prepared above was measured according to the solubility measurement in Preparation Example 1, which was 324.30 mg/mL, 44,000 times that of neratinib maleate.

TABLE 2

| No. | Ratio (W/W) |
|---|---|
| 4 | API:HP-β-CD = 1:2.5 |

Example 3

An appropriate amount of neratinib maleate (API) was transferred to 40 times (W/W) of an aqueous hydrochloric acid solution (pH 1.2). The mixture was stirred until the solids were completely dissolved, and appropriate amounts of HP-β-cyclodextrin and PCL-PVAc-PEG were added to the resultant solution. The mixture was stirred at room temperature for 30 mins or more to give a clear solution or a suspension. The solution or suspension was then lyophilized to give a loose powder, which was then aliquoted into capsules.

The solubility of the ternary clathrate of neratinib, HP-β-cyclodextrin, and PCL-PVAc-PEG prepared above was measured according to the solubility measurement in Preparation Example 1. The results are shown in Table 3.

TABLE 3

| No. | Formula | Ratio (w/w) | API solubility (mg/mL) | Increasing factor (×10,000) |
|---|---|---|---|---|
| 5 | API + HP-β-CD + PCL-PVAc-PEG | 1:1.1:0.25 | 251.05 | 3.4 |
| 6 | API + HP-β-CD + PCL-PVAc-PEG | 1:2.3:0.25 | 316.75 | 4.3 |
| 7 | API + HP-β-CD + PCL-PVAc-PEG | 1:2.5:0.25 | 429.75 | 5.8 |
| 8 | API + HP-β-CD + PCL-PVAc-PEG | 1:4.6:0.25 | 509.95 | 6.9 |
| 9 | API + HP-β-CD + PVP VA64 | 1:2.5:0.25 | 405.45 | 5.5 |
| 10 | API + HP-β-CD + PEG 4000 | 1:2.5:0.25 | 389.20 | 5.3 |

It can be seen from the above results that when the mass ratio of neratinib maleate to HP-β-cyclodextrin to PCL-PVAc-PEG was 1:1.1:0.25, the solubility of the resultant clathrate was 251.05 mg/mL, 34,000 times that of the neratinib maleate substance, and the solubility of the resultant clathrate increased along with the increase in the amount of HP-β-cyclodextrin. In the same ratio, the solubility contributions of polymers PCL-PVAc-PEG, PVP VA64, and PEG4000 to the ternary system were compared, and the results show that the solubilization effect of PCL-PVAc-PEG was the highest, while those of the other two polymers were slightly lower but better than that of the binary system clathrate (API+HP-β-CD).

Example 4

An appropriate amount of neratinib maleate (API) was transferred to 40 times (W/W) of an aqueous hydrochloric acid solution (pH 1.2). The mixture was stirred until the solids were completely dissolved, and appropriate amounts of HP-β-cyclodextrin and PCL-PVAc-PEG were added to the resultant solution in a mass ratio shown in Table 4. The mixture was stirred at room temperature for 30 mins or more to give a clear solution. The solution was then subjected to spray drying to give a loose powder with the same conditions as in Example 1. The dried powder was then aliquoted into capsules in a loading amount of 40 mg.

TABLE 4

| No. | Formula | Ratio (w/w) | API solubility (mg/mL) | Increasing factor (×10,000) |
|---|---|---|---|---|
| 10 | API + HP-β-CD + PCL-PVAc-PEG | 1:2.5:0.25 | 421.32 | 5.7 |

Example 5

An appropriate amount of neratinib maleate (API) was transferred to 40 times (W/W) of an aqueous hydrochloric acid solution (pH 1.2). The mixture was stirred until the solids were completely dissolved, and PCL-PVAc-PEG was added to the resultant solution in a neratinib maleate-to-PCL-PVAc-PEG mass ratio of 1:0.25. The mixture was stirred at room temperature for 30 mins or more to give a clear solution or a suspension. The solution or suspension was then lyophilized to give a loose powder, which was then aliquoted into capsules in a loading amount of 37 mg.

The solubility of the clathrate of neratinib and PCL-PVAc-PEG was measured according to the solubility measurement in Preparation Example 1. The results are shown in Table 5.

TABLE 5

| No. | Formula | API solubility (mg/mL) | Increasing factor (×10,000) |
|---|---|---|---|
| 11 | API+PCL-PVAc-PEG | 48.01 | 0.65 |

It can be seen from the results in Tables 2-5 that the solubility of the ternary clathrate formed by neratinib maleate, HP-β-cyclodextrin, and PCL-PVAc-PEG was greater than the sum of the solubilities of the binary clathrates of neratinib maleate and HP-β-cyclodextrin or PCL-PVAc-PEG, suggesting a good synergic effect.

Example 6

X-ray powder diffraction patterns of clathrate Nos. 7 and 10 were obtained. It can be seen that the clathrate Nos. 7 and 10 were both amorphous, wherein the conditions for PXRD detection are as follows: the 2θ detection range was 5-90°, and the rate was 5°/min.

The DSC patterns of clathrate Nos. 7 and 10 were analyzed. It can be seen that neratinib maleate had an endothermic peak at 198-207° C., HP-β-cyclodextrin had endothermic peaks at 93-113° C. and 253-317° C., and the clathrates exhibited endothermic peaks at 184-246° C. and 219-240° C., suggesting the formation of cyclodextrin clathrates. The DSC detection conditions are as follows: the test temperature range was 30-350° C., and the ramping rate was 10° C./min.

Example 7

The formulations were innovator formulation Nos. 1, 2, 3 and 7, a commercial originator product, and a control formulation of 40 mg/tablet.

Figure 1:
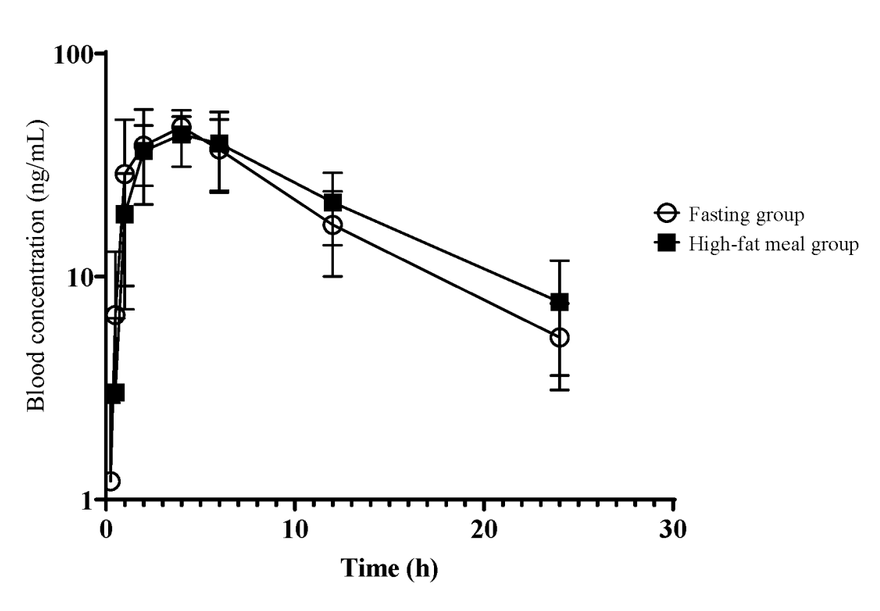
FIG. 1 shows plasma exposure of neratinib in fasting and high-fat meal conditions.

The animals were divided into 3 groups: a fasting group (group A) and a high-fat meal group (group B) both receiving the innovator formulations, and a high-fat meal group (group C) receiving the commercial originator product. Each group included 4 adult beagle dogs (2 females and 2 males) of 9-11 kg. The study protocol included 2×2 crossover treatment sessions, with 1 washout period between each session. Animals in the fasting group were deprived of food for 12 h, while the high-fat meal groups were administrated 30 min after the meal. The formula and calorie distribution of the high-fat meal are detailed in Table 6. The regimen for beagle dogs was oral administration once daily, 2 capsules/tablets per dose. Blood samples were collected at 0.25, 0.5, 1, 2, 4, 6, 12, and 24 h post-dose, and PK analysis results are detailed in Table 7 and FIG. 1.

TABLE 6

| Total energy (kcal) | 800-1000 |
| Energy in fat | 500-600 |
| Energy ratio in fat (%) | ≥50% |
| High-fat meal formula | Two butter-basted eggs (100 g of eggs, 15 g of butter) Two pieces of bacon (50 g) Two pieces of buttered toast (20 g of butter, 2 × 30 g of toast) 113 g of mashed potatoes 240 mL of whole milk |

It can be seen from the results in Table 7 that the $AUC_{0-24h}$ (ng*h/mL) ratio of the high-fat meal group to the fasting group for the innovator formulation Nos. 2 and 3 was between 0.81-1.19, while the Cmax (ng/mL) ratio was between 0.92-0.95, indicating that the formulation Nos. 2 and 3 can eliminate the food effects and reduce the dietary requirements for administration. In high-fat meal groups, compared with the originator product, formulation No. 7 showed a normalized $AUC_{0-24h}$ (ng*h/mL)/(mg/kg) ratio (B/C) of 0.93 and a normalized Cmax (ng/mL)/(mg/kg) ratio (B/C) of 1.03, suggesting that the relative bioavailability of F3 is comparable to that of the commercial originator product, and the efficacies of the two formulations are equivalent at the same dose.

Example 8

The gastrointestinal irritation was observed in a beagle animal model sensitive to gastrointestinal reactions, and the used formulations were innovator formulation Nos. 1, 2, 3 and 7, a commercial originator product, and a control formulation of 40 mg/tablet.

4 adult beagle dogs (2 females and 2 males) of 9 to 11 kg were treated for 2 consecutive days and observed for the development of diarrhea on the days of administration. For the originator product, 6 beagle dogs (3 females and 3 males) of 9 to 11 kg were treated for 2 consecutive days and observed for development of diarrhea on the days of administration. The results are shown in Table 8. The regimen for beagle dogs was oral administration once daily, 2 capsules/tablets per dose.

TABLE 7

| | | $T_{max}$ (h) | $C_{max}$ (ng/mL) | $AUC_{0-24h}$ (ng * h/mL) | $C_{max}$ (ng/mL)/ Does (mg/kg) | $AUC_{0-24h}$ (ng * h/mL)/ Dose (mg/kg) |
| --- | --- | --- | --- | --- | --- | --- |
| Commercial originator | High-fat meal group (C) | 5 | 49.8 | 615 | 6.23 | 76.9 |
| No. 1 | Fasting group (A) | 3.33 | 65.7 | 591 | / | / |
| | High-fat meal group (B) | 4 | 101 | 1009 | 11.0 | 110 |
| | Ratio (B/A) | 1.20 | 1.54 | 1.71 | / | / |
| | Ratio (B/C) | 0.8 | / | / | 1.77 | 1.43 |
| No. 2 | Fasting group (A) | 3 | 38.1 | 460 | / | / |
| | High-fat meal group (B) | 4.5 | 41.4 | 568 | 5.21 | 71.4 |
| | Ratio (B/A) | 1.5 | 0.92 | 0.81 | / | / |
| | Ratio (B/C) | 0.9 | / | / | 0.84 | 0.93 |
| No. 3 | Fasting group (A) | 4.5 | 98.1 | 714 | / | / |
| | High-fat meal group (B) | 4 | 93.4 | 849 | 10.3 | 93.3 |
| | Ratio (B/A) | 0.89 | 0.95 | 1.19 | / | / |
| | Ratio (B/C) | 0.8 | / | / | 1.66 | 1.21 |
| No. 7 | Fasting group (A) | 4 | 51.6 | 489 | / | / |
| | High-fat meal group (B) | 3.5 | 48.5 | 535 | 6.41 | 71.3 |
| | Ratio (B/A) | 0.88 | 0.94 | 1.09 | / | / |
| | Ratio (B/C) | 0.7 | / | / | 1.03 | 0.93 |

TABLE 8

Incidence of diarrhea in beagle dogs receiving different formulations

| Parameters | Commercial originator product | No. 1 | No. 2 | No. 3 | No. 7 |
|---|---|---|---|---|---|
| Included animals | 6 | 4 | 4 | 4 | 4 |
| Animals with diarrhea | 4 | 4 | 0 | 4 | 0 |
| Incidence of diarrhea | 67% | 100% | 0% | 100% | 0% |

The above study demonstrates that for the commercial originator product, the incidence of diarrhea in beagle dogs was 67%, while in the neratinib-cyclodextrin composition group, no diarrhea events were observed. The results suggest that the composition can significantly reduce or eliminate the irritation of the drug to gastrointestinal tracts, thereby eliminating the adverse event diarrhea.

Example 9 (Comparison in Different Acids)

1 g of neratinib maleate (API) was transferred to 40 mL of an aqueous acetic acid solution (pH 2.2) or 40 mL of an aqueous citric acid solution (pH 1.75). The mixtures were stirred until the solids were completely dissolved, and 2.5 g of HP-β-cyclodextrin was added to the resultant solution in an API: HP-β-cyclodextrin (w/w) ratio of 1:2.5. The mixtures were stirred at room temperature for 30 min or more to give clear solutions. The solution was then subjected to spray drying to give a loose powder. The inlet temperature of the solution was 200° C., the flow rate was 5.2 mL/min, and the outlet temperature was 100-130° C.

The solubility and phenomenon of the clathrate of neratinib and HP-β-cyclodextrin prepared was measured according to the solubility measurement in Preparation Example 1, and compared with a formulation sample (No. 2) prepared with hydrochloric acid in Example 1.

| Acid species | PH | API solubility (mg/mL) | Phenomenon |
|---|---|---|---|
| Hydrochloric acid | 1.2 | 360.31 | Immediate dissolution; clear viscous solution |
| Acetic acid | 2.2 | 28 | Immediate dissolution; crystallization after 10 min |
| Citric acid | 1.75 | 1252.13 | Immediate dissolution; clear sviscou solution |

Since the solubility of neratinib maleate is pH dependent, a low pH (less than or equal to 2.4) may be beneficial to the dissolution of the drug substance into free API, thereby accelerating the complexation with cyclodextrin. From the above study, it can be seen that although the API can be dissolved in different acids at a low pH, the formed cyclodextrin clathrates have different dissolution capacities and states. The clathrate prepared from citric acid has the best solubilizing capacity for the drug. However, as a weak acid, a higher amount of citric acid may be consumed to prepare an aqueous solution with a low pH (1.75) and thus an API-to-citric acid mass ratio in the clathrate of 1:2.8 (W/W), which is very unfavorable for the weight control of the tablet. As a strong acid, hydrochloric acid only requires a small amount to reduce the pH to 1.2, where the mass ratio of API to hydrochloric acid is only 1:0.13 (W/W). The clathrate formed by acetic acid exhibited poor stability and produced crystal precipitates during the dissolution process.

It should be noted that the above-mentioned preferred examples are further, non-limiting, and detailed descriptions of the embodiments of the present invention, and are only for illustrating the technical concepts and features of the present invention. They are provided for better understanding and implementation of the present invention by those skilled in the art, rather than limiting the scope of the present invention. All equivalent changes and modifications made according to the spirit of the present invention should fall within the protection scope of the present invention.

The invention claimed is:

1. A formulation of neratinib, comprising an active ingredient comprising a therapeutically effective amount of neratinib thereof, or a pharmaceutically acceptable salt thereof, or a hydrate thereof, and cyclodextrin, wherein the active ingredient and the cyclodextrin are in a ratio ranging from 1:2.5 to 1:4.0 by weight, wherein the active ingredient is neratinib maleate and the cyclodextrin is 2-hydroxypropyl-β-cyclodextrin (HP-β-cyclodextrin).

2. The formulation of claim 1, wherein the neratinib maleate and the HP-β-cyclodextrin are in a ratio ranging from 1:2.5 to 1:3.0 by weight.

3. The formulation of claim 1, wherein the neratinib maleate and the HP-β-cyclodextrin are in a ratio ranging from about 1:3.0 to about 1:4.0 by weight.

4. The formulation of claim 1, wherein the neratinib maleate and the HP-β-cyclodextrin are in a ratio ranging from about 1:2.5 to about 1:3.2 by weight.

5. The formulation of claim 1, wherein the amounts of the neratinib maleate and the HP-β-cyclodextrin are selected so that the formulation is characterized by a ratio between a first $AUC_{o\text{-}24h}$ and a second $AUC_{o\text{-}24h}$ ranging from about 0.8:1 to about 1.6:1, wherein the first $AUC_{o\text{-}24h}$ is obtained when the formulation is administered once a day with high fat diet, and wherein the second $AUC_{o\text{-}24h}$ is obtained when the formulation is administered once a day under fasting condition, wherein the first AUCo-24 h and the second AUCo-24 h are obtained from the same daily dose of the active ingredient.

6. The formulation of claim 5, wherein the ratio between the first $AUC_{o\text{-}24h}$ and the second $AUC_{o\text{-}24h}$ ranges from about 0.8:1 to about 1:1, wherein the neratinib maleate and the HP-β-cyclodextrin are in a ratio ranging from 1:2.5 to 1:3.0 by weight.

7. The formulation of claim 5, wherein the ratio between the first $AUC_{o\text{-}24h}$ and the second $AUC_{o\text{-}24h}$ ranges from about 1:1 to about 1.6:1, wherein the neratinib maleate and the HP-β-cyclodextrin are in a ratio ranging from 1:3.0 to 1:4.0 by weight.

8. The formulation of claim 1, comprising the active ingredient ranging from about 200 mg to about 300 mg.

9. The formulation of claim 1, wherein the amounts of the neratinib maleate and the HP-β-cyclodextrin are selected so that the formulation is characterized by a ratio between a first $C_{max}$ and a second $C_{max}$ ranging from about 0.9:1 to about 1.3:1, wherein the first $C_{max}$ is obtained when the formulation is administered once a day with high fat diet, and wherein the second $C_{max}$ is obtained when the formulation is administered once a day under fasting condition, wherein the first $C_{max}$ and the second $C_{max}$ are obtained from the same daily dose of the active ingredient.

10. The formulation of claim 1, wherein the neratinib maleate and the HP-β-cyclodextrin form a clathrate.

11. The formulation of claim 1, wherein the formulation further comprises polyvinyl caprolactam-polyvinyl acetate-polyethylene glycol graft copolymer (PCL-PVAc-PEG).

12. The formulation of claim 11, wherein the ratio by weight between neratinib maleate and PCL-PVAc-PEG in the formulation ranges from about 1:0.2 to about 1:0.3.

13. The formulation of claim 12, wherein the neratinib maleate and the HP-β-cyclodextrin are in a ratio ranging from about 1:3.0 to about 1:4.0 by weight.

14. The formulation of claim 12, wherein the neratinib maleate and the HP-β-cyclodextrin are in a ratio ranging from about 1:2.5 to about 1:3.2 by weight.

15. The formulation of claim 1, wherein the amounts of neratinib maleate and HP-β-cyclodextrin are selected so that the formulation has less than 50% chance of diarrhea when administered once a day to a subject.

16. A method of reducing risk of diarrhea in a human patient being treated with neratinib, comprising administering to the subject a formulation of claim 1.

17. A method of treating breast cancer in a human patient, comprising administering to the subject a formulation of claim 1.

18. A formulation of neratinib, comprising an active ingredient comprising a therapeutically effective amount of neratinib thereof, or a pharmaceutically acceptable salt thereof, or a hydrate thereof, PCL-PVAc-PEG, and cyclodextrin, wherein the active ingredient and the cyclodextrin are in a ratio ranging from about 1:1.6 to about 1:5.0 by weight, wherein the active ingredient is neratinib maleate and the cyclodextrin is HP-β-cyclodextrin, wherein the ratio by weight between neratinib maleate and PCL-PVAc-PEG in the formulation ranges from about 1:0.2 to about 1:0.3.

19. The formulation of claim 18, wherein the neratinib maleate and the HP-β-cyclodextrin are in a ratio ranging from about 1:3.0 to about 1:4.0 by weight.

20. The formulation of claim 18, wherein the neratinib maleate and the HP-β-cyclodextrin are in a ratio ranging from about 1:2.5 to about 1:3.2 by weight.

\* \* \* \* \*